United States Patent
Muzik et al.

(10) Patent No.: US 11,852,622 B2
(45) Date of Patent: Dec. 26, 2023

(54) METHODS FOR AVOIDING IMPROPER MIXING OF ADDITIVES IN A REFUELING STORAGE TANK AND DEVICES THEREFOR

(71) Applicant: FAUDI Aviation Americas, Colorado Springs, CO (US)

(72) Inventors: Tom Muzik, Colorado Springs, CO (US); Marcus Wildschuetz, Colorado Springs, CO (US)

(73) Assignee: FAUDI AVIATION AMERICAS, Colorado Springs, CO (US)

(*) Notice: Subject to any disclaimer, the term of this patent is extended or adjusted under 35 U.S.C. 154(b) by 173 days.

(21) Appl. No.: 17/490,133

(22) Filed: Sep. 30, 2021

(65) Prior Publication Data
US 2023/0097176 A1    Mar. 30, 2023

(51) Int. Cl.
*G01N 33/28*    (2006.01)
*B60K 15/03*    (2006.01)

(52) U.S. Cl.
CPC ......... *G01N 33/2835* (2013.01); *B60K 15/03* (2013.01); *B60K 2015/0321* (2013.01); *B60K 2015/03348* (2013.01)

(58) Field of Classification Search
CPC ............... G01N 33/2835; B60K 15/03; B60K 2015/0321; B60K 2015/03348
See application file for complete search history.

(56) References Cited

U.S. PATENT DOCUMENTS

| | | | |
|---|---|---|---|
| 5,988,439 A | 11/1999 | Webb | |
| 2006/0278283 A1 | 12/2006 | Gouzou et al. | |
| 2009/0315729 A1* | 12/2009 | Inhoffer | B64F 1/28 340/632 |
| 2014/0294606 A1 | 10/2014 | Anderson | |
| 2021/0107782 A1 | 4/2021 | Swanek et al. | |

OTHER PUBLICATIONS

International Search Report and Written Opinion for PCT/US2021/052823, dated Jan. 18, 2022.

* cited by examiner

*Primary Examiner* — Jacob M Amick
(74) *Attorney, Agent, or Firm* — Troutman Pepper Hamilton Sanders LLP (Rochester)

(57) ABSTRACT

A method of preventing improper mixing of additives in a refueling storage tank includes receiving, by a computing device, data related to an additive introduced to the refueling storage tank from a sensor positioned in the refueling storage tank. The additive introduced to the refueling tank is determined, by the computing device, based on the data received from the sensor. An output is provided, by the computing device, when the determined additive does not match a predetermined additive for the refueling storage tank. Devices and systems for preventing improper mixing of additives in a refueling storage tank are also disclosed.

20 Claims, 2 Drawing Sheets

---

Receive data related to an additive introduced to refueling storage tank 300

↓

Determine additive introduced to the storage tank 302

↓

Provide output when the determined additive does not match a predetermined additive for the storage tank 304

METHODS FOR AVOIDING IMPROPER MIXING OF ADDITIVES IN A REFUELING STORAGE TANK AND DEVICES THEREFOR

FIELD

The present technology relates to methods for avoiding improper mixing of additives in a refueling storage tank and devices thereof. More particular, the present technology relates to methods for avoiding mixing of diesel exhaust fluid and fuel system icing inhibitor in a refueling storage tank and devices therefor.

BACKGROUND

Various additives may be employed to assist in the operation of diesel engines for vehicles, such as aircrafts. Two such additives include diesel exhaust fluid (DEF) and fuel system icing inhibitor (FSII).

DEF is a clear, non-toxic liquid used to reduce the amount of air pollution created by a diesel engine. Specifically, DEF is an aqueous urea solution made with 32.5% urea and 67.5% deionized water. Diesel engines can be run with a lean burn air-to-fuel ratio to ensure the full combustion of soot and to prevent their exhausting unburnt fuel. The excess air necessarily leads to generation of nitrogen oxides ($NO_x$), which are harmful pollutants, from the nitrogen in the air. DEF is consumed in selective catalytic reduction (SCR) that lowers the concentration of $NO_x$ in the diesel exhaust emissions released into the atmosphere from a diesel engine. DEF from a separate tank is injected into the exhaust pipeline. Within the SCR catalyst, the $NO_x$ are reduced by the ammonia into water and nitrogen, which are both non-polluting. The water and nitrogen are then released into the atmosphere through the exhaust.

FSII is an additive to aviation fuels that prevents the formation of ice in fuel lines. Jet fuel can contain a small amount of dissolved water that does not appear in droplet form. As an aircraft gains altitude, the temperature drops and the jet fuel's capacity to hold water is diminished. Dissolved water can separate out and could become a serious problem if it freezes in fuel lines or filters, blocking the flow of fuel and shutting down an engine. FSII is mixed with jet fuel as it is pumped into the aircraft. The mixture of FSII must be between 0.10% and 0.15% by volume for the additive to work correctly, and the FSII must be distributed evenly throughout the fuel. Simply adding FSII after the fuel has been pumped is therefore not sufficient. As the aircraft climbs after takeoff, the temperature drops, and any dissolved water will separate out from the fuel. FSII dissolves itself in water preferentially over the jet fuel, where it then serves to depress the freezing point of water to –43° C. Since the freezing point of jet fuel itself is usually in this region, the formation of ice is now a minimal concern.

At airports, where DEF can sometimes be required for diesel ground service vehicles, its labelling and storage must be carefully managed to avoid accidentally servicing jet aircraft with DEF instead of fuel system icing inhibitor FSII, a mistake that has been attributed to multiple in-flight engine failure and grounding incidents. In particular, when mixed with jet fuel, DEF will react with certain chemical components of the fuel to form crystalline deposits within the fuel system. These crystalline deposits can then accumulate in filters, engine fuel nozzles, and fuel metering components resulting in a loss of engine power and potential flameout.

Due to their physical similarities in color, clarity and odor, it is difficult to distinguish between DEF and FSII. If their containers are similar in size and shape, are not clearly labeled, or if the two products are not stored separately, there is a risk that DEF might be inadvertently be identified as FSII and added to the icing inhibitor tank on a refueling truck or dispenser truck and subsequently introduced to the fuel system of an aircraft. Thus, there is the possibility that refueling tanks on refueling vehicles may be improperly loaded with the incorrect additive, which can have catastrophic results.

Current solutions solution to the potential contamination problem is one of prevention, including storage restrictions and operator training. However, these solutions do not eliminate the potential for operator error to lead to improper contamination. Thus, more efficient and effective methods are needed to prevent the introduction of DEF directly into jet fuel in place of FSII.

The present technology is directed to overcoming these and other deficiencies in the art.

SUMMARY

One aspect of the present technology relates to a method of preventing improper mixing of additives in a refueling storage tank. The method includes receiving, by a computing device, data related to an additive introduced to the refueling storage tank from a sensor positioned in the refueling storage tank. The additive introduced to the refueling tank is determined, by the computing device, based on the data received from the sensor. An output is provided, by the computing device, when the determined additive does not match a predetermined additive for the refueling storage tank.

Another aspect of the present technology relates to a system for preventing improper mixing of additives in a refueling storage tank. The system includes a sensor positioned in a refueling storage tank configured to provide data related to an additive introduced to the refueling storage tank. A computing device or programmable hardware logic is coupled to the sensor and is configured to receive data related to an additive introduced to the refueling storage tank from the sensor. The additive introduced to the refueling tank is determined based on the data received from the sensor. An output is provided when the determined additive does not match a predetermined additive for the refueling storage tank.

Yet a further aspect of the present technology relates to refueling truck or dispenser truck that includes one or more a storage tanks configured to receive one or more additives. A sensor is positioned in at least one of the one or more refueling storage tanks. The sensor is configured to provide data related to an additive introduced to the at least one of the one or more refueling storage tanks. A computing device or programmable hardware logic is coupled to the sensor and is configured to receive data related to an additive introduced to the at least one of the refueling storage tanks from the sensor. The additive introduced to the refueling tank is determined based on the data received from the sensor. An output is provided when the determined additive does not match a predetermined additive for the refueling storage tank.

The present technology provides a number of advantages including avoiding improper mixing of additives and/or avoiding improper introduction of an additive into the fuel system of a vehicle, such as an aircraft. The present technology provides additional safety measures that are more effective at preventing such improper mixing of additives with fuel that provide an additional layer of protection beyond mere preventative measures such as training and storage restrictions.

DETAILED DESCRIPTION

The present technology relates to methods for avoiding improper mixing of additives in a refueling storage tank and devices thereof.

One aspect of the present technology relates to refueling truck or dispenser truck that includes one or more a storage tanks configured to receive one or more additives. A sensor is positioned in at least one of the one or more refueling storage tanks. The sensor is configured to provide data related to an additive introduced to the at least one of the one or more refueling storage tanks. A computing device or programmable hardware logic is coupled to the sensor and is configured to receive data related to an additive introduced to the at least one of the refueling storage tanks from the sensor. The additive introduced to the refueling tank is determined based on the data received from the sensor. An output is provided when the determined additive does not match a predetermined additive for the refueling storage tank.

Figure 1:
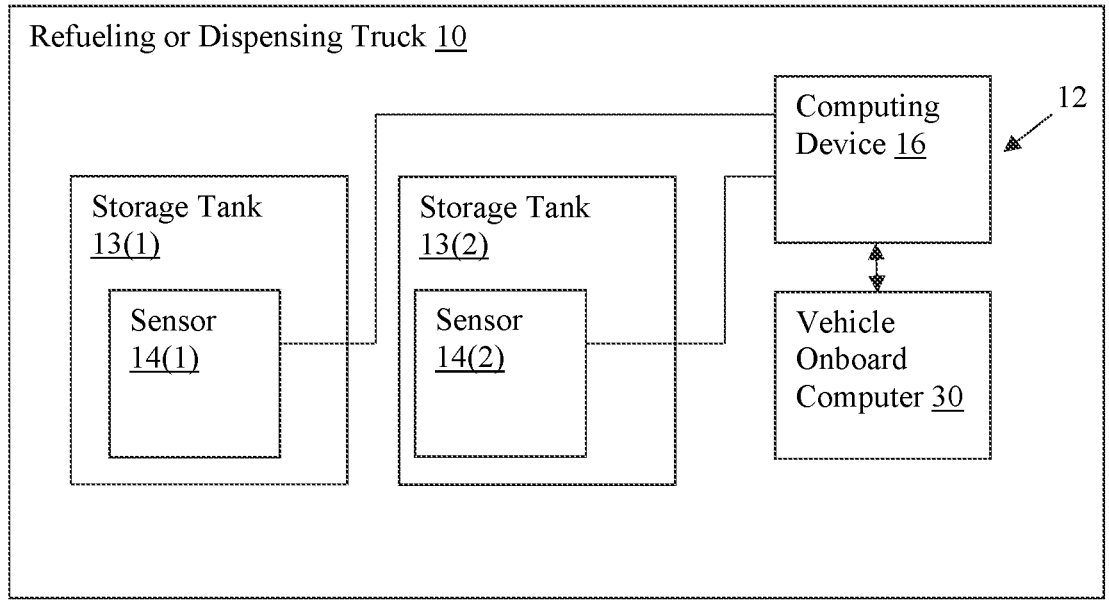
FIG. 1 is a block diagram of an exemplary refueling vehicle including a system of the present technology for preventing improper mixing of additives in refueling tanks located thereon.

FIG. 1 is a block diagram of an exemplary refueling vehicle 10 that includes a system 12 for avoiding improper mixing of additives in refueling storage tanks 13(1) and/or 13(2) located thereon. Although two storage tanks are illustrated and described it is to be understood that other numbers and/or types of storage tanks could be located on the refueling vehicle 10, including a single storage tank for providing an additive. Refueling vehicle 10 may be employed, for example, at an airport to provide one or more additives to an aircraft, although refueling vehicle 10 may be utilized for other purposes. Refueling vehicle 10 may be any system used for refueling purposes that includes one or more storage tanks for delivering additives and the use of the term vehicle is not intended to be limiting.

In this example, storage tanks 13(1) and 13(2) are sized and configured to receive one or more additives, such as diesel exhaust fluid (DEF) or fluid system icing inhibitor (FSII), although storage tanks 13(1) and/or 13(2) may be used for other additives. Storage tanks 13(1) and 13(2) may be any storage tanks known in the art to safely and securely handle the desired additives to be provided to a vehicle, such as an aircraft, and may be constructed of any suitable materials. In one example, storage tanks 13(1) and 13(2) are configured to have a small reservoir located at an entrance thereof for receiving a fluid additive. The reservoir allows for a concentration of the additive being added to be present in the reservoir for distinguishing from a liquid already present in the storage tank.

Another aspect of the present technology relates to a system for preventing improper mixing of additives in a refueling storage tank. The system includes a sensor positioned in a refueling storage tank configured to provide data related to an additive introduced to the refueling storage tank. A computing device or programmable hardware logic is coupled to the sensor and is configured to receive data related to an additive introduced to the refueling storage tank from the sensor. The additive introduced to the refueling tank is determined based on the data received from the sensor. An output is provided when the determined additive does not match a predetermined additive for the refueling storage tank.

Referring again to FIG. 1, system 12 includes sensors 14(1) and 14(2) located within storage tanks 13(1) and 13(2), respectively, and each coupled to a computing device 16 to provide data thereto, although the present technology may be employed using a single sensor in a single storage tank. As described in further detail below, computing device 16 may be embodied as programmable hardware logic. System 12 can include other types and/or numbers of elements such as additional electronics, such as analog to digital converters or amplifiers, by way of example, in other combinations. System 12 provides a number of advantages including providing a system configured to determine an additive introduced to the storage tanks 13(1) and/or 13(2) to avoid improper mixing of additives or to avoid improper introduction of an additive into the fuel system of a vehicle, such as an aircraft. For example, system 12 can be utilized to prevent the introduction of DEF directly into jet fuel in place of FSII, although system 12 can be used for other purposes.

In this example, sensors 14(1) and 14(2) are positioned in the storage tanks 13(1) and 13(2), respectively to measure one or more properties of an additive supplied within the storage tank. Sensors 14(1) and 14(2) can be located in the storage tanks 13(1) and 13(2) respectively, such that sensors 14(1) and 14(2) come into contact with, or are located proximate to, a flow of fluid additive introduced into the storage tanks 13(1) and 13(2), respectively. In one example, sensors 14(1) and 14(2) are located proximate to an opening of the storage tanks 13(1) and 13(2), for example in a reservoir located at an entrance thereof for receiving a fluid additive. The reservoir allows for a concentration of the additive being added to be present in the reservoir for distinguishing from a liquid already present in the storage tank.

Sensors 14(1) and/or 14(2) can be any sensor configured to differentiate one or more features between one or more additives of interest, such as DEF and FSII, by way of example. For example, sensors 14(1) and 14(2) can be each be one of a density sensor, a refractometer, a tension meter, a frequency sweep sensor, a temperature sensor, a resistance sensor, or a capacitive sensor, or combinations thereof, although other suitable sensors may be employed. Sensors 14(1) and 14(2) measure values related to properties of the additive and provide data related to the one or more liquid additives to provide for differentiation between one or more additives of interest, such as DEF and FSII, as described in further detail below.

In this example, sensors 14(1) and 14(2) are coupled to computing device 16 to provide data to the computing device 16 during operation, as described in further detail below, although a single sensor can be coupled to the computing device in other examples of the present technology. Sensors 14(1) and/or 14(2) may be coupled to computing device 16 in any suitable manner to allow the transfer of data between sensors 14(1) and 14(2) and the computing device 16. As discussed above, system 12 may include additional electronics that allow for the transfer of data between sensors 14(1) and 14(2) and computing device 16.

Figure 2:
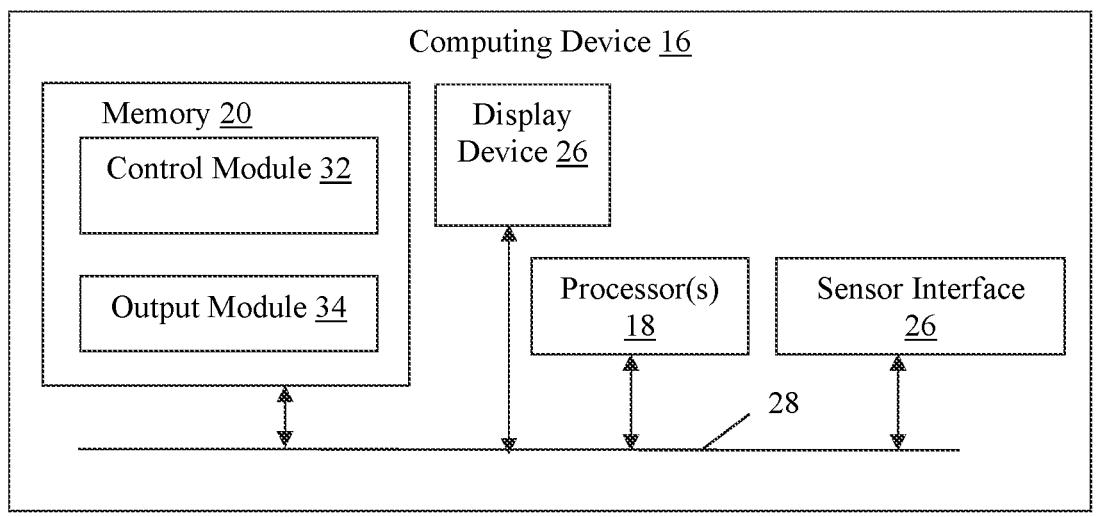
FIG. 2 is a block diagram of the exemplary computing device shown in FIG. 1.

Referring to FIG. 2, a block diagram of an exemplary computing device 16 of the system 12 is illustrated. In this particular example, the computing device 16 includes processors 18, a memory 20, a sensor interface 22, and a display device 26, which are coupled together by a bus 28 or other communication link, although the computing device 16 can include other types and/or numbers of systems, devices, components and/or other elements in other configurations. In other examples, computing device 16 may be a programmable logic controller coupled to the sensors 14(1) and/or 14(2) to provide a latching relay configured to shut down the refueling vehicle 10 when improper mixing of additives is detected, as described with respect to the methods described herein.

Referring again to FIG. 2, the processor(s) 18 of the computing device 16 may execute programmed instructions stored in the memory 20 of the computing device 16 for the any number of the functions and other operations illustrated and described herein. The processor(s) 18 may include one or more CPUs or general purpose processors with one or more processing cores, for example, although other types of processor(s) can also be used. In other examples, the processors 18 can include a microcontroller, a reduced instruction set architecture (RISC) processor, configurable hardware logic (e.g., a field programmable gate array (FPGA) or a programmable logic controller (PLC)), and/or any combination of such processing devices. Accordingly, while processor(s) 18 and separate memory 20 coupled via a bus 28 are included in the example illustrated in FIG. 2 and described herein, other architectures can also be used.

The memory 20 of the computing device 16 stores the programmed instructions for one or more aspects of the present technology as described and illustrated herein, although some or all of the programmed instructions could be stored elsewhere. A variety of different types of memory storage devices, such as random access memory (RAM), read only memory (ROM), flash memory, or other computer readable medium which is read from and written to by a magnetic, optical, or other reading and writing system that is coupled to the processor(s) 18, can be used for the memory 20. The memory 20 of the computing device 16 can store one or more applications that can include executable instructions that, when executed by the processors 18, cause the computing device 16 to perform actions, such as to communicate with the sensors 14(1) and 14(2) or with the a vehicle onboard computing device 30, for example, and to perform other actions as described and illustrated by way of the examples herein.

Accordingly, the examples may also be embodied as one or more non-transitory computer readable media, such as the memory 20 of the computing device 16, having instructions stored thereon for one or more aspects of the present technology as described and illustrated herein. The instructions in some examples include executable code that, when executed by one or more processing devices, such as the processor(s) 18 of the computing device 16, cause the processing devices to carry out steps necessary to implement the methods of the examples of this technology that are described and illustrated herein.

The memory 20 of the computing device 16 in these particular examples includes a control module 32 and an output module 34. The control module 32 is configured to process input from the sensors 14(1) and 14(2) to determine an additive sensed by the sensors 14(1) and 14(2). The output module 34 is configured to communicate sensed or determined parameters to the display device 26, as described and illustrated in more detail below. The display device 26 can be an LED display, for example, although other types of displays can also be used in other examples.

The sensor interface 22 of the computing device 16 operatively couples and communicates with the sensors 14(1) and 14(2) of the system 12. Accordingly, the sensor interface 22 obtains signals from the sensors 14(1) and 14(2) that are communicated to the control module 32 to facilitate determination of one or more properties of the additive introduced into the storage tank, as described in further detail below.

Yet a further aspect of the present technology relates to a refueling truck or dispenser truck that includes one or more a storage tanks configured to receive one or more additives. A sensor is positioned in at least one of the one or more refueling storage tanks. The sensor is configured to provide data related to an additive introduced to the at least one of the one or more refueling storage tanks. A computing device or programmable hardware logic is coupled to the sensor and is configured to receive data related to an additive introduced to the at least one of the refueling storage tanks from the sensor. The additive introduced to the refueling tank is determined based on the data received from the sensor. An output is provided when the determined additive does not match a predetermined additive for the refueling storage tank.

Figure 3:
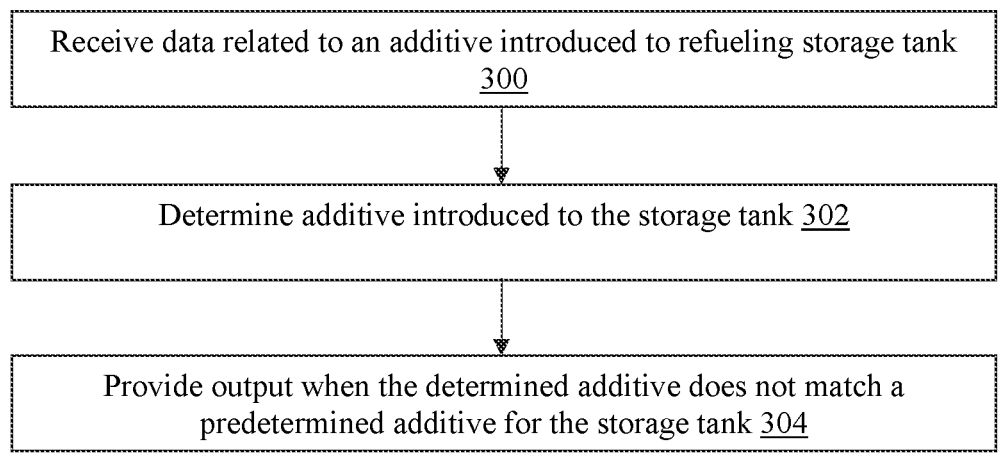
FIG. 3 is a flowchart of an exemplary method of preventing improper mixing of additives in a refueling tank of the present technology.

Referring to FIG. 3, a flow diagram of an exemplary method of operation of the computing device 16 of the system 12 is illustrated. As described above, the computing device, in one example, can be a programmable logic controller (PLC) configured to perform the method described below. The method may be advantageously employed to avoid improper mixing, or storage, of additives in a refueling storage tank.

In step 300, computing device 16 receives data related to an additive introduced to the at least one of the refueling storage tanks 13(1) or 13(2) from the corresponding sensor 14(1) and/or 14(2). For example, sensors 14(1) and 14(2) can be each be one of a density sensor, a refractometer, a tension meter, a frequency sweep sensor, a temperature sensor, a resistance sensor, or a capacitive sensor, or combinations thereof, although other suitable sensors may be employed. Sensors 14(1) and 14(2) measure values related to properties of the additive and provide data related to the one or more liquid additives to provide for differentiation between one or more additives of interest, such as DEF and FSII. In one example, the data related to the additive is collected by the sensors 14(1) and/or 14(2) and sent to the computing device 16 through sensor interface 22. Sensors 14(1) and 14(2) may be located at an entrance to the storage tanks 13(1) and 13(2), respectively, so that the properties of the additive introduced may be determined as the additive is introduced into the storage tanks.

In step 302, the computing device 16 determines the additive introduced to the storage tank 13(1) and/or 13(2) based on the data received from the sensor. In one example, the computing device 16 compares the data related to the additive introduced received from the sensor 14(1) and/or 14(2) to corresponding stored data related to a plurality of additives. The corresponding data may be stored, for example, in memory 20. The computing device 16 determines the additive based on a match between the data related to the additive and corresponding data related to one of the plurality of additives stored in the memory 20. For example, the following table provides data that can be stored in the memory 20 that can be used to differentiate between DEF and FSII, although other data tables may be employed for other additives. Any appropriate sensors may be employed to determine the values set forth below in order to differentiate between DEF and FSII.

| | | |
|---|---|---|
| Density [g/cm$^3$] + 15° C. | 1.09 | 1.023 |
| Refractive index | 1,383 (31%) | 1,424 (52%) |
| Surface tension [mN/m] | 65 | 39 |
| Frequency Sweep CH1 [%] | 15 | 37.8 |
| Frequency Sweep CH2 [mA] | 6.37 | 10 |
| Dynamic Viscosity [mPa * s] | 1.4 | N.A. |
| Electrical resistance [Ω] (7.5 cm) | 0.6k | 4M |
| Exothermic reaction 20° C. 50:50 | Temperature increase from 20° C. to 35 ° C | |
| Exothermic reaction 40° C. 50:50 | Temperature increase from 40° C. to 55 ° C | |

In step 304, the computing device 16 provides an output through the output module 34 when the determined additive does not match a predetermined additive for the refueling storage tank stored in the memory 20. The computing device 16 is configured to identify the particular sensor from which the data is received and correlate that sensor to a predetermined additive for the associated storage tank. In one example, the output is provided when the additive is diesel exhaust fluid and the predetermined additive for the refueling storage tank is fuel system icing inhibitor, or vice versa, although outputs may be provided based on other types of additives. The output, for example, can include one or more instructions from the output module 34 to disable operation of the refueling vehicle 10 provided to the ignition system of the vehicle. In another example, the output is an auditory or visual alarm provided through display device 26. In other examples, the output may be provided to the vehicle onboard computing device 30 to provide a visual or audio output using the lights and or horn of the vehicle.

As described and illustrated by way of the example herein, this technology provides a relatively low-cost system that can be easily introduced to a refueling truck or dispenser truck to provide alarms, safety shutoffs, and functional displays to enable effective and efficient methods of preventing the addition of an improper additive into a storage tank thereof. The system of this technology is advantageously capable of avoiding the improper mixing of additives into, for example, a fuel system to avoid the harmful results associated therewith.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method of preventing improper additive mixing, the method implemented by a computing device and comprising:
receiving data related to an additive introduced to a refueling storage tank from a sensor positioned in the refueling storage tank;
comparing the data related to the additive introduced to the refueling storage tank received from the sensor to corresponding stored data related to a plurality of additives;
determining the additive introduced to the refueling tank based on a match between the data related to the additive introduced to the refueling storage tank received from the sensor and the corresponding data related to one of the plurality of additives; and
providing an output when the determined additive does not match a predetermined additive for the refueling storage tank.

2. The method of claim 1, wherein the sensor comprises a density sensor, a refractometer, a tension meter, a frequency sweep sensor, a temperature sensor, a resistance sensor, or a capacitive sensor.

3. The method of claim 1, wherein the additive is one of diesel exhaust fluid or fuel system icing inhibitor.

4. The method of claim 3, further comprising providing the output when the additive is diesel exhaust fluid and the predetermined additive for the refueling storage tank is fuel system icing inhibitor.

5. The method of claim 3 further comprising providing the output when the additive is fuel system icing inhibitor and the predetermined additive for the refueling storage tank is diesel exhaust fluid.

6. The method of claim 1, wherein the output is an auditory or visual alarm.

7. The method of claim 1, wherein the refueling storage tank is located on a refueling vehicle and the output comprises one or more instructions to disable operation of the refueling vehicle.

8. The method of claim 1, wherein the sensor is positioned in a reservoir located at an opening of the refueling storage tank.

9. A system, comprising:
a sensor positioned in a refueling storage tank configured to provide data related to an additive introduced to the refueling storage tank; and
a computing device or programmable hardware logic coupled to the sensor and configured to:
receive data related to an additive introduced to the refueling storage tank from the sensor;
determine the additive introduced to the refueling tank based on the data received from the sensor; and
provide an output when the determined additive does not match a predetermined additive for the refueling storage tank, wherein the determined additive is diesel exhaust fluid and the predetermined additive for the refueling storage tank is fuel system icing inhibitor.

10. The system of claim 9, wherein the sensor comprises a density sensor, a refractometer, a tension meter, a frequency sweep sensor, a temperature sensor, a resistance sensor, or a capacitive sensor.

11. The system of claim 9, wherein the sensor is located proximate an opening in the refueling storage tank.

12. The system of claim 9, wherein the computing device or programmable hardware logic is further configured to:
compare the data related to the additive introduced to the refueling storage tank to corresponding stored data related to a plurality of additives; and determine the additive based on a match between the data related to the additive and corresponding data related to one of the plurality of additives.

13. The system of claim 9, wherein the output is an auditory or visual alarm.

14. The system of claim 9, wherein the refueling storage tank is located on a refueling vehicle and the output comprises one or more instructions to disable operation of the refueling vehicle.

15. The system of claim 9, wherein the sensor is positioned in a reservoir located at an opening of the refueling storage tank.

16. A refueling or dispenser truck, comprising:
one or more a storage tanks configured to receive one or more additives;
a sensor positioned in at least one of the one or more refueling storage tanks configured to provide data related to an additive introduced to the at least one of the one or more refueling storage tanks; and
a computing device or programmable hardware logic coupled to the sensor and configured to:
receive data related to an additive introduced to the at least one of the refueling storage tanks from the sensor;
determine the additive introduced to the refueling tank based on the data received from the sensor; and
provide an output when the determined additive does not match a predetermined additive for the refueling storage tank, wherein the determined additive is fuel system icing inhibitor and the predetermined additive for the refueling storage tank is diesel exhaust fluid.

17. The refueling or dispenser truck of claim 16, wherein the sensor comprises a density sensor, a refractometer, a tension meter, a frequency sweep sensor, a temperature sensor, a resistance sensor, or a capacitive sensor.

18. The refueling or dispenser truck of claim 16, wherein each of the one or more storage tanks has a sensor positioned therein.

19. The refueling or dispenser truck of claim 16, wherein the output comprises one or more instructions to disable operation of the refueling or dispenser truck.

20. The refueling or dispenser truck of claim 16, wherein the sensor is positioned in a reservoir located at an opening of the at least one of the one or more refueling storage tanks.

* * * * *